United States Patent
Li

(10) Patent No.: US 12,004,718 B2
(45) Date of Patent: Jun. 11, 2024

(54) DEVICE AND METHODS FOR COLOR CORRECTED OCT IMAGING ENDOSCOPE/CATHETER/CAPSULE TO ACHIEVE HIGH-RESOLUTION

(71) Applicant: THE JOHNS HOPKINS UNIVERSITY, Baltimore, MD (US)

(72) Inventor: Xingde Li, Ellicott City, MD (US)

(73) Assignee: The John Hopkins University, Baltimore, MD (US)

( * ) Notice: Subject to any disclaimer, the term of this patent is extended or adjusted under 35 U.S.C. 154(b) by 161 days.

(21) Appl. No.: 16/481,248

(22) PCT Filed: Jan. 26, 2018

(86) PCT No.: PCT/US2018/015374
§ 371 (c)(1),
(2) Date: Jul. 26, 2019

(87) PCT Pub. No.: WO2018/140683
PCT Pub. Date: Aug. 2, 2018

(65) Prior Publication Data
US 2020/0000327 A1      Jan. 2, 2020

Related U.S. Application Data

(60) Provisional application No. 62/451,299, filed on Jan. 27, 2017.

(51) Int. Cl.
*A61B 1/04* (2006.01)
*A61B 1/00* (2006.01)
(Continued)

(52) U.S. Cl.
CPC .......... *A61B 1/041* (2013.01); *A61B 1/00117* (2013.01); *A61B 1/00172* (2013.01);
(Continued)

(58) Field of Classification Search
CPC ............ A61B 1/00117; A61B 1/00172; A61B 1/00188; G02B 27/4227
See application file for complete search history.

(56) References Cited

U.S. PATENT DOCUMENTS 4,641,927 A * 2/1987 Prescott ............... G02B 3/0087
                                                      359/654
6,099,146 A * 8/2000 Imamura ................. F21V 13/04
                                                      359/558
(Continued)

FOREIGN PATENT DOCUMENTS

| JP | 2005323874 A | 11/2005 |
|---|---|---|
| WO | 2013177154 A1 | 11/2013 |
| WO | 2015054243 A1 | 4/2015 |

OTHER PUBLICATIONS

Gora, et al., Tethered capsule endomicroscopy enables less-invasive imaging of gastrointestinal tract microstructure. Nat Med. Feb. 2013; 19(2): 238-240.
(Continued)

*Primary Examiner* — John P Leubecker
*Assistant Examiner* — Jae Woo

(57) ABSTRACT

The present invention is directed to an achromatic capsule endoscope with diffractive optics. A micromotor (or a broadband rotary joint) and a custom 800 nm SD-OCT system make ultrahigh-resolution 3D volumetric imaging over a large area possible. The diffractive microlens is used directly with other miniature lens including but not limited to a GRIN lens, making the capsule endoscope design simpler and cost effective. Preliminary ex vivo 3D intraluminal imaging was performed with the distal-scanning capsule endoscope in conjunction with a home-built broadband spectral-domain OCT system, demonstrating the performance of the diffractive capsule. Considering the miniature OCT capsule imaging probe is an attractive component for (Continued)

using the OCT technology for esophagus imaging (or other internal organs), the proposed approach will have a broad impact on endoscopic OCT imaging by improving OCT resolution in any applications that involve a capsule OCT probe, such as gastrointestinal (GI) tract imaging, airway imaging etc.

18 Claims, 8 Drawing Sheets

(51) Int. Cl.
*A61B 5/00* (2006.01)
*G02B 27/42* (2006.01)
(52) U.S. Cl.
CPC ........ *A61B 1/00188* (2013.01); *A61B 5/0066* (2013.01); *G02B 27/4227* (2013.01)

(56) References Cited

U.S. PATENT DOCUMENTS

| | | | |
|---|---|---|---|
| 6,181,481 B1* | 1/2001 | Yamamoto | G02B 9/12 359/558 |
| 6,687,010 B1* | 2/2004 | Horii | G01B 9/0201 356/479 |
| 7,530,948 B2 | 5/2009 | Seibel et al. | |
| 7,692,797 B2* | 4/2010 | Kawahara | A61B 5/0066 356/497 |
| 7,733,584 B2* | 6/2010 | Kazakevich | G02B 23/2407 359/793 |
| 7,907,352 B2* | 3/2011 | Miyano | G02B 23/243 359/754 |
| 7,952,718 B2* | 5/2011 | Li | G01B 9/02091 356/479 |
| 8,018,598 B2* | 9/2011 | Cense | G01B 9/02091 356/456 |
| 9,084,564 B2* | 7/2015 | Bublitz | A61B 3/107 |
| 9,161,684 B2 | 10/2015 | Seibel et al. | |
| 10,095,020 B2* | 10/2018 | Tearney | G02B 23/2423 |
| 10,584,954 B2* | 3/2020 | Tearney | G01B 9/02038 |
| 10,646,105 B2* | 5/2020 | Li | A61B 5/0066 |
| 10,736,494 B2* | 8/2020 | Gora | A61B 5/0066 |
| 10,852,121 B2* | 12/2020 | Vakoc | G01K 11/32 |
| 2003/0142934 A1 | 7/2003 | Pan et al. | |
| 2004/0254474 A1* | 12/2004 | Seibel | A61B 5/0066 600/473 |
| 2005/0280794 A1* | 12/2005 | Tsuji | G03F 7/70566 355/67 |
| 2007/0038119 A1 | 2/2007 | Chen et al. | |
| 2009/0009771 A1* | 1/2009 | Ostrovsky | G01B 9/02032 356/479 |
| 2010/0157308 A1* | 6/2010 | Xie | A61B 5/6852 356/477 |
| 2011/0007321 A1* | 1/2011 | Everett | A61B 3/102 356/479 |
| 2011/0222020 A1* | 9/2011 | Izatt | G01B 9/02091 351/205 |
| 2012/0176613 A1* | 7/2012 | Marple | G01J 3/0208 356/301 |
| 2012/0229813 A1* | 9/2012 | Kim | G01J 3/12 356/479 |
| 2013/0310643 A1* | 11/2013 | Gora | A61B 1/041 600/109 |
| 2015/0077760 A1* | 3/2015 | Koerner | G01B 9/02008 356/496 |
| 2015/0289752 A1 | 10/2015 | Rachlin et al. | |
| 2016/0227990 A1 | 8/2016 | Li et al. | |
| 2016/0317228 A1* | 11/2016 | Fermann | A61B 90/20 |
| 2018/0259317 A1* | 9/2018 | Tearney | A61B 5/0066 |
| 2021/0161373 A1* | 6/2021 | Tearney | A61B 1/06 |
| 2021/0196113 A1* | 7/2021 | Copland | A61B 3/0091 |

OTHER PUBLICATIONS

Liang, et al., Ultrahigh speed en face OCT capsule for endoscopic imaging. Biomed Opt Express. Apr. 1, 2015; 6(4): 1146-1163.

Xi, et al., Diffractive catheter for ultrahigh-resolution spectral-domain volumetric OCT imaging. Opt Lett. Apr. 1, 2014;39 (7):2016-9.

* cited by examiner

DEVICE AND METHODS FOR COLOR CORRECTED OCT IMAGING ENDOSCOPE/CATHETER/CAPSULE TO ACHIEVE HIGH-RESOLUTION

CROSS-REFERENCE TO RELATED APPLICATIONS

This application is a 35 U.S.C. § 371 U.S. national entry of International Application PCT/US2018/015374, having an international filing date of Jan. 26, 2018, which claims the benefit of U.S. Provisional Application No. 62/451,299, filed Jan. 27, 2017, the content of each of the aforementioned applications is herein incorporated by reference in their entirety.

GOVERNMENT SUPPORT

This invention was made with government support under grant numbers CA153023 and HL121788, awarded by the National Institutes of Health. The government has certain rights in the invention.

FIELD OF THE INVENTION

The present invention relates generally to medical imaging. More particularly, the present invention relates to a device and method for color corrected OCT imaging.

BACKGROUND OF THE INVENTION

OCT is a noninvasive, high-resolution optical imaging technology capable of real-time imaging of tissue microanatomy with a few millimeter imaging depth and can be envisioned as an optical analog of ultrasound B-mode imaging, except that it utilizes near infrared light rather sound waves. Compared to ultrasound, OCT does not require a matching gel and the resolution of OCT can be 50-100 times finer than ultrasound. OCT can thus function as a form of "optical biopsy", capable of assessing tissue microanatomy and function with a resolution approaching that of standard histology but without the need for tissue removal. The axial resolution of OCT is governed by the spectral bandwidth of the light source and it is inversely proportional to the source spectrum bandwidth. Chromatic aberration in the OCT imaging optics will alter the backreflected spectrum from the target, resulting in the loss of OCT axial resolution. The change in the backreflected spectrum from the sample could also result in the increase in the side lobes of the OCT imaging signal, which again will lead to the loss of OCT axial resolution. In addition, as in conventional imaging optics, the chromatic aberration will focus light of different colors to different spots, thus degrading the OCT lateral resolution as well. In a benchtop imaging system such as a microscope, chromatic aberration in the imaging optics is routinely corrected by using achromatic lenses (e.g. lenses made of multi elements with different refractive index profiles and surface curvatures). But, such approaches are not cost effective or practical to be implemented in miniature OCT imaging probes.

Miniature endoscopes are a critical component in the OCT technology, enabling translational applications for imaging internal luminal organs such as the gastrointestinal tract or airways. Most OCT endoscopes developed so far were designed for imaging at 1300 nm, which provides 2-3 mm imaging depth and 8-30 μm axial resolution. However, there is an increasing need to develop an ultrahigh-resolution OCT endoscope for resolving fine structures (e.g. under 5 μm) such as airway smooth muscle or structural changes associated with early stage diseases. Benefiting from the availability of broadband light sources at 800 nm, ultrahigh-resolution OCT imaging has been demonstrated at such wavelength with bench-top systems. For the endoscopic setting, due to the challenges such as management of chromatic aberration over a broadband spectral bandwidth, there are only few achromatic endoscopic setups. The designs in those endoscopes are rather complicated and expensive, involving multi-element achromatic microlenses.

Accordingly, there is a need in the art for a miniature OCT device and a cost-effective and practically implemented method for color corrected OCT imaging.

SUMMARY

The foregoing needs are met, to a great extent, by the present invention which provides a device for obtaining OCT images from a subject including a miniature OCT capsule imaging probe configured to obtain high-resolution images of the subject and a diffraction element configured to mitigate wavelength dependent aberration in the high-resolution images obtained by the OCT imaging probe.

In accordance with an aspect of the present invention, the diffraction element includes a diffractive lens. The diffractive lens is positioned at a distal end of a compound lens within the OCT capsule probe. The diffractive lens can have a high diffraction efficiency over a broad spectral range, such as approximately 750 to approximately 950 nm (but not limited to this range). The wavelength dependent aberration takes the form of a chromatic aberration.

In accordance with another aspect of the present invention a method for mitigating achromatic aberration in OCT imaging includes using a diffraction element integrated into miniature imaging optics of an OCT capsule probe, wherein the OCT capsule probe comprises a broadband light source. The method also includes reducing a longitudinal focal shift of the broadband light source, such that different colors of light in the broadband light source will be focused to a small spot for achieving high lateral resolution. Additionally, the method includes minimizing distortion to a backreflected spectral at a given imaging depth, such that OCT axial resolution is improved to an optimal axial resolution afforded by the broadband light source.

In accordance with yet another aspect of the present invention, a device for obtaining OCT images from a subject includes a miniature OCT capsule imaging probe configured to obtain ultrahigh-resolution images of the subject, a micrometer beam scanner, and a diffraction optics configured to mitigate wavelength dependent aberration in the high-resolution images obtained by the OCT capsule imaging probe.

According to yet another aspect of the present invention, a device for obtaining OCT images from a subject includes a miniature OCT capsule probe to obtain ultrahigh-resolution images of the subject, a fiber-optic rotary joint, and diffraction optics configured to mitigate wavelength dependent aberration in the high-resolution images obtained by the OCT capsule imaging probe.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and.

DETAILED DESCRIPTION OF THE PREFERRED EMBODIMENTS

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to an achromatic endoscope which employs a diffractive microlens. Along with a micromotor (or a broadband rotary joint) and a custom 800 nm SD-OCT system, ultrahigh-resolution 3D volumetric imaging over a large area becomes possible. The diffractive microlens can be used directly with a GRIN lens or other miniature optics, making the capsule endoscope design simpler and cost effective. Preliminary ex vivo 3D intraluminal imaging was performed with the capsule endoscope in conjunction with a home-built broadband spectral-domain OCT system, demonstrating the performance of the diffractive capsule endoscope. Considering the miniature OCT imaging probe is the required component for using the OCT technology in internal organs, the proposed approach will have a broad impact on endoscopic OCT imaging by improving OCT resolution in any applications that involve an capsule OCT probe, such as gastrointestinal (GI) tract imaging, airway imaging etc.

Figure 1:
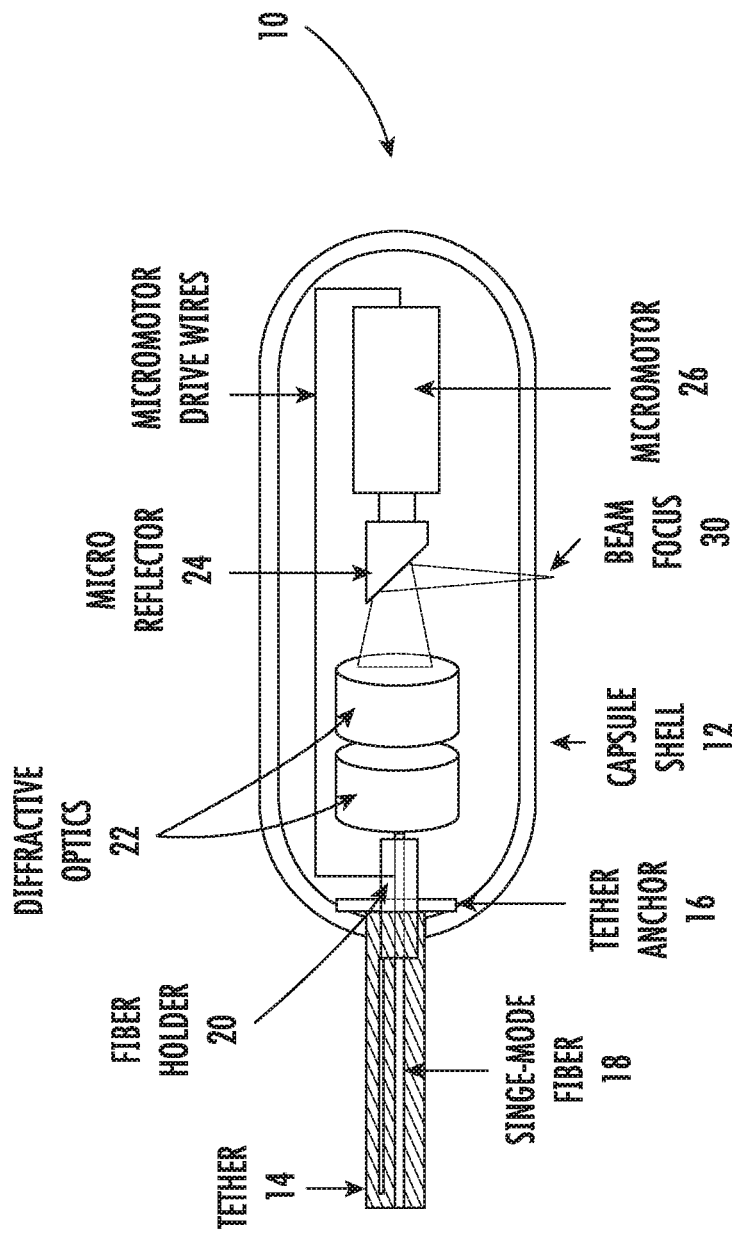
FIG. 1 illustrates a schematic diagram of a distal end of a distal-scanning OCT capsule probe.

FIG. 1 illustrates a schematic diagram of a distal end design for a distal-scanning OCT capsule imaging probe 10, which entails (not limited to) a capsule shell 12, a tether 14, a tether anchor 16, a single-mode optical fiber (SMF) 18, a fiber holder 20, miniature diffractive optics (and a holder with the holder not shown) 22, a micro beam reflector 24, and a micromotor (and a holder with the holder not shown) 26. Correction of chromatic aberration in the miniature imaging probes becomes very challenging due to the probe size (diameter and rigid length) and cost restriction. Although the concept of using a multi-element lens similar to a microscope objective can be introduced to the miniature OCT imaging probes for correcting the chromatic aberration (as we demonstrated before), that approach would be very challenging and impractical due to prohibitive cost and increased probe size. FIG. 1 also illustrates the point of the beam focus 30 after the beam is reflected off of microreflector 24.

The present invention provides a solution to overcome the long-existing problem of chromatic aberration in miniature OCT probes by introducing a diffractive element/mask to the imaging optics. The diffractive element will diffract light of different wavelengths to slightly different directions, which effectively changes the beam path for each wavelength. With a proper design, the path changes induced by the diffractive element/mask can be opposite to the changes caused by chromatic aberration, thus compensating the chromatic aberration.

Figure 2:
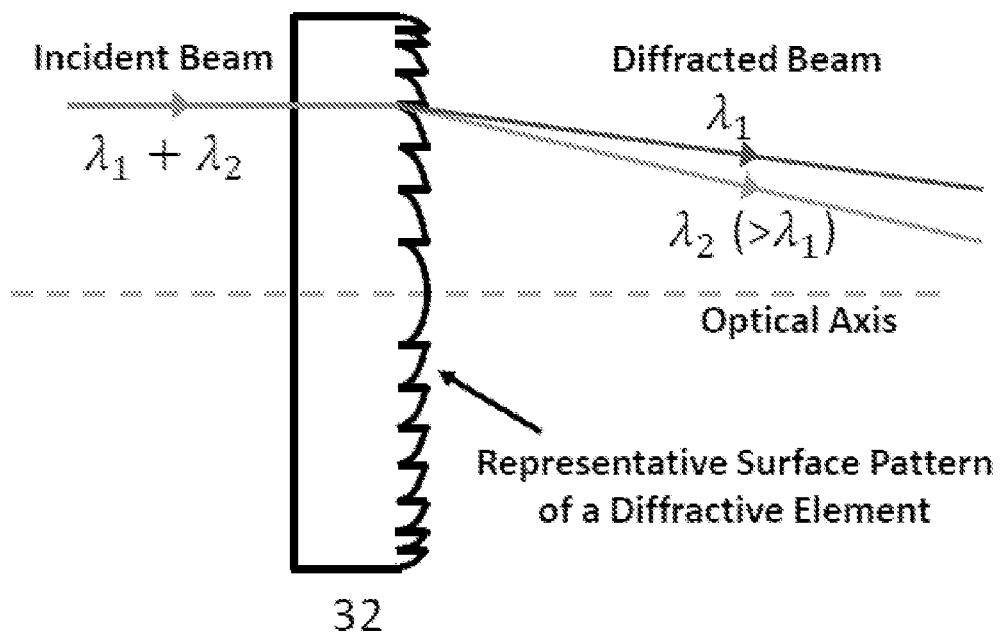
FIG. 2 illustrates a schematic diagram of a representative pattern of a diffractive element or mask, according to an embodiment of the present invention.

FIG. 2 illustrates a representative schematic of such a diffractive element/mask for use with an OCT probe according to the present invention. In this design, the longer wavelength can be bent more towards the optical axis, which is opposite from the chromatic aberration effect. The diffractive element/mask 32 can be made very small in size and very large in quantity (through mass microfabrication), and it can be easily introduced to the imaging optics of an OCT probe at its distal end, e.g. by sandwiching between some optics or attached to the end of the a lens. As illustrated in FIG. 2 a longer wavelength ($\lambda_2$) will be bent more towards the optical axis than shorter wavelength ($\lambda_1$) which is opposite from what occurs in chromatic aberration. Thus, the combination of such a diffractive element with a focus lens can mitigate chromatic aberration.

Figure 3:
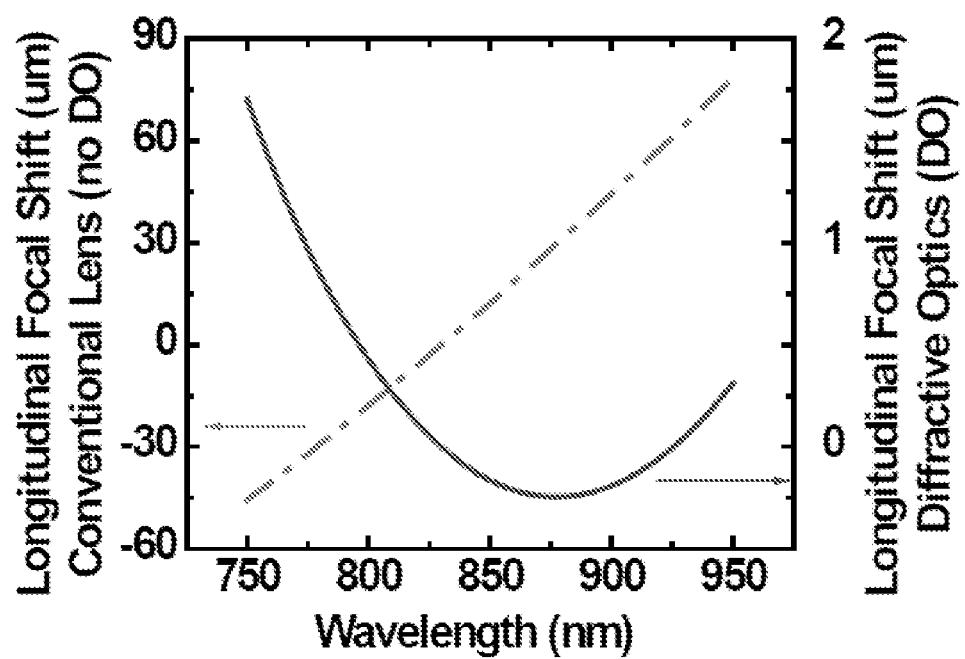
FIG. 3 illustrates a graphical representation of a longitudinal focal shift of the capsule endoscope made of conventional (dashed line) and diffractive (solid line) optics.

Simulations have been performed to investigate the performance of the proposed approach. As shown in FIG. 3, the chromatic aberration of a typical compound lens-based OCT capsule imaging probe, represented by the longitudinal focal shift, is about 110 um. When a properly designed diffractive element is added to the distal end optics of the capsule imaging probe, the chromatic aberration is dramatically reduced, resulting in a much smaller longitudinal focal shift down to 2 um. FIG. 3 illustrates a graphical view of a longitudinal focal shift for a conventional compound lens based OCT capsule imaging probe (dashed line) and for a diffractive OCT capsule imaging probe which has a built-in diffractive element (solid line) over the wavelength range of 750-950 nm. Longitudinal focal shift represents the severity of chromatic aberration in an imaging probe. It is noticed that the longitudinal focal shift is reduced by about 50 times (i.e. from about 110 μm down to about 2 μm) when using diffractive optics, showing the effective correction of chromatic correction by the diffractive element.

The proposed approach is demonstrated by implementing a customized diffractive element to a miniature OCT capsule imaging probe. To demonstrate the feasibility of the proposed concept, the spectra backreflected from a mirror placed at the focal plane of the imaging probe was measured and also measured at other parallel planes with a given distance away from the focal plane. In an ideal case (i.e. for an imaging probe without any chromatic aberration), the backreflected spectra should not change much with the mirror position.

Figure 4:
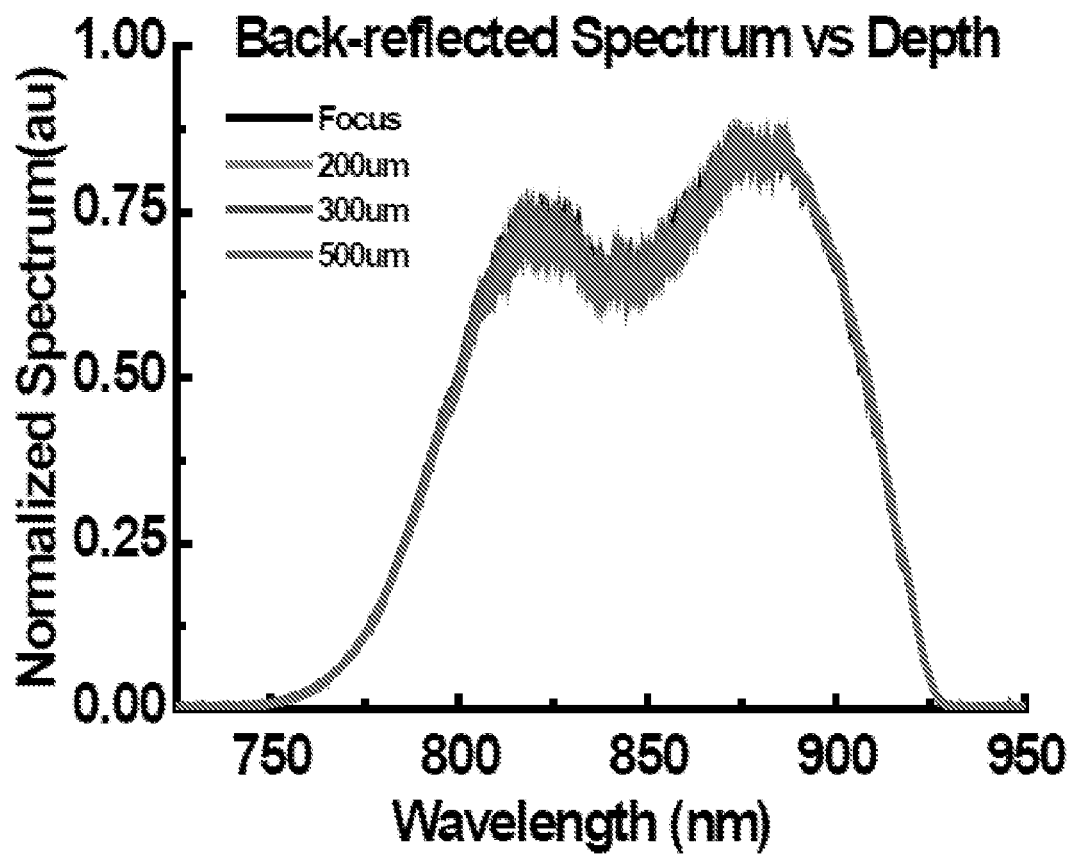
FIG. 4 illustrates a graphical view of spectra backreflected by a mirror placed at a focal plane and planes 200 um, 300 um and 500 um away from the focal plane for a conventional optics-based OCT capsule probe and for a diffractive OCT capsule probe.

FIG. 4 illustrates a graphical view of the spectra backreflected from a mirror placed at the focal plane and parallel planes 200 um, 300 um, and 500 um away from the focal plane. The spectra experienced negligible changes when the mirror was moved away from the focal plane along imaging depth, suggesting superb achromatic performance of the proposed approach based on diffractive optics.

Figure 5:
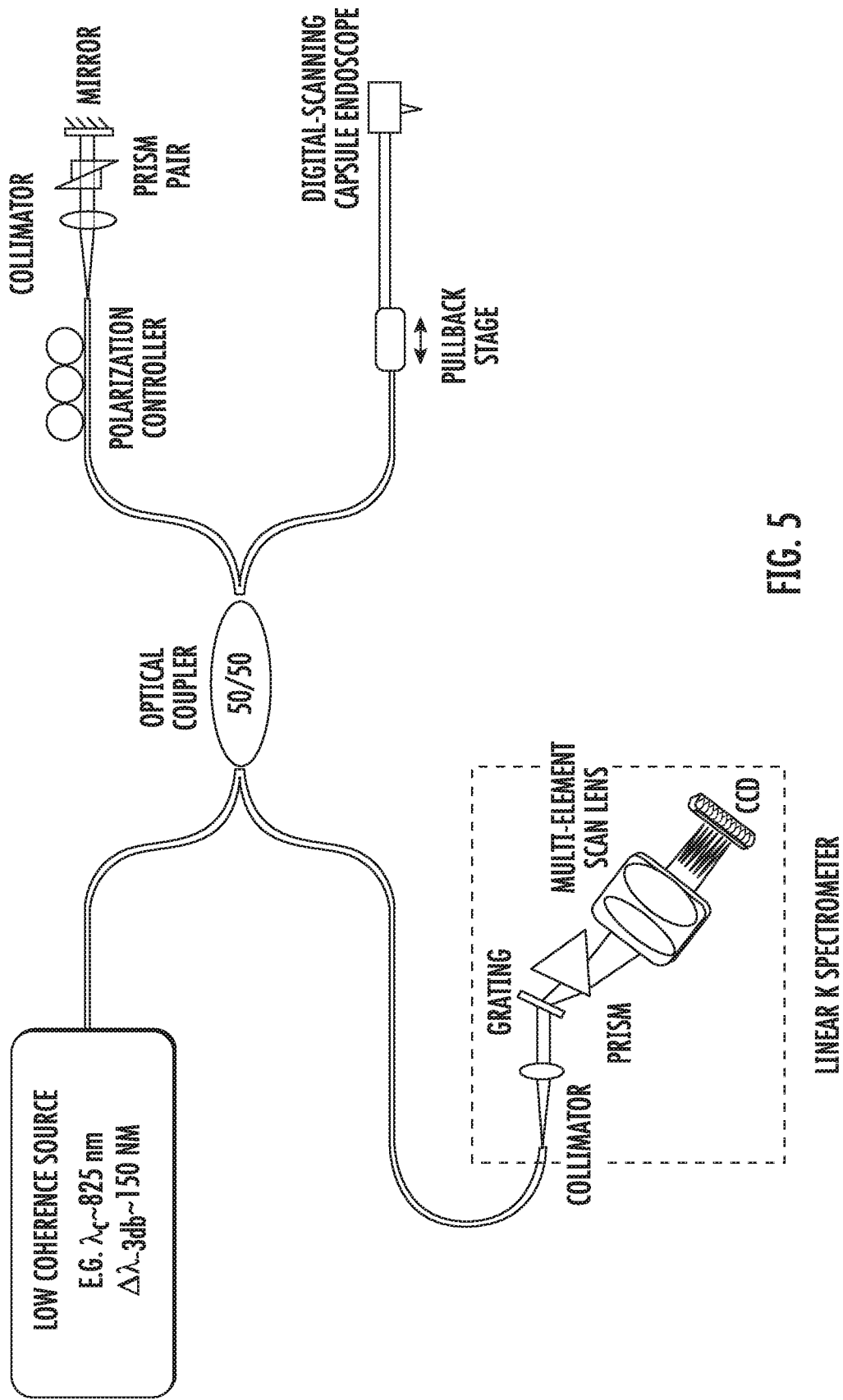
FIG. 5 illustrates a schematic diagram of an 800 nm broadband distal-scanning capsule SC-OCT imaging system.

FIG. 5 illustrates a schematic a home-built SD-OCT imaging system that can be used with the distal-scanning, diffractive capsule imaging probe, where a broadband low coherence light source (such as a short pulsed Ti:Sapphire laser) with a 3 dB spectral bandwidth (e.g. of ~150 nm centering at 825 nm) is employed as the light source. The light source is delivered into the sample and reference arms through a broadband 50/50 fiber coupler. In the sample arm, the tether of the capsule probe is mounted on a translational stage to enable pullback for 3D volumetric imaging. In order to match the dispersion in two arms, a prism pair was inserted into reference arm. The residual dispersion mismatch between the two arms can be numerically compensated. For detection, a custom-designed, home-built linear-in-wavenumber spectrometer is employed. The line scan camera has 2048 pixels and a maximum line scan rate of 70 k/second at 12 bit resolution. Real-time OCT imaging is rendered by a custom C++ program, which controls the system synchronization, real-time data acquisition, signal processing, data storage, etc. The prototype capsule with the diffractive lens was measured to have a 2.6 µm axial resolution in air and a 12.5 µm lateral resolution.

Figure 6A:
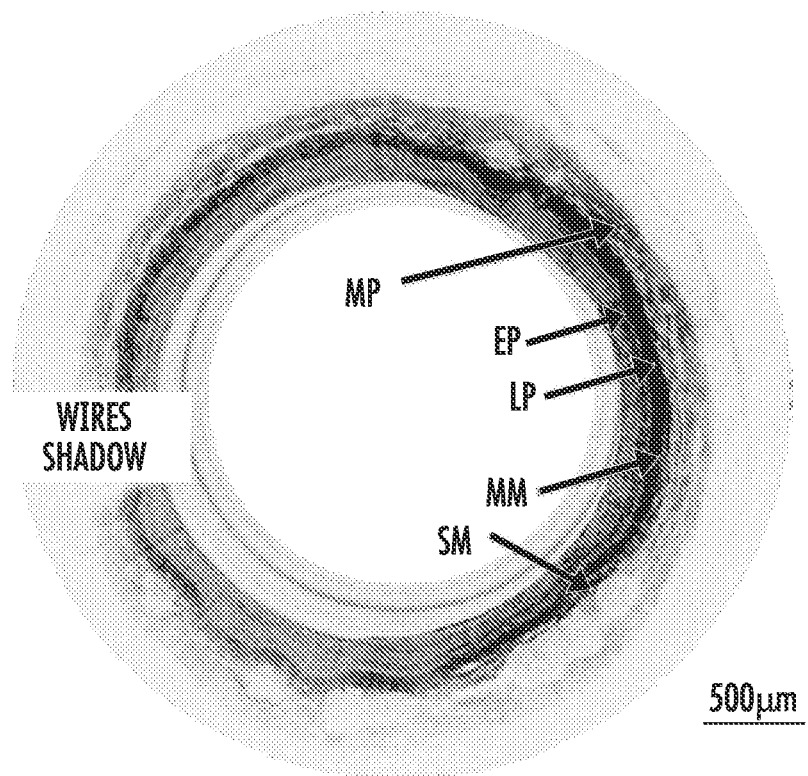
FIGS. 6A-B illustrate a representative image of pig esophagus ex vivo acquired by the diffractive OCT capsule endoscope along with an 800 nm broadband SC-OCT system.
Figure 6B:
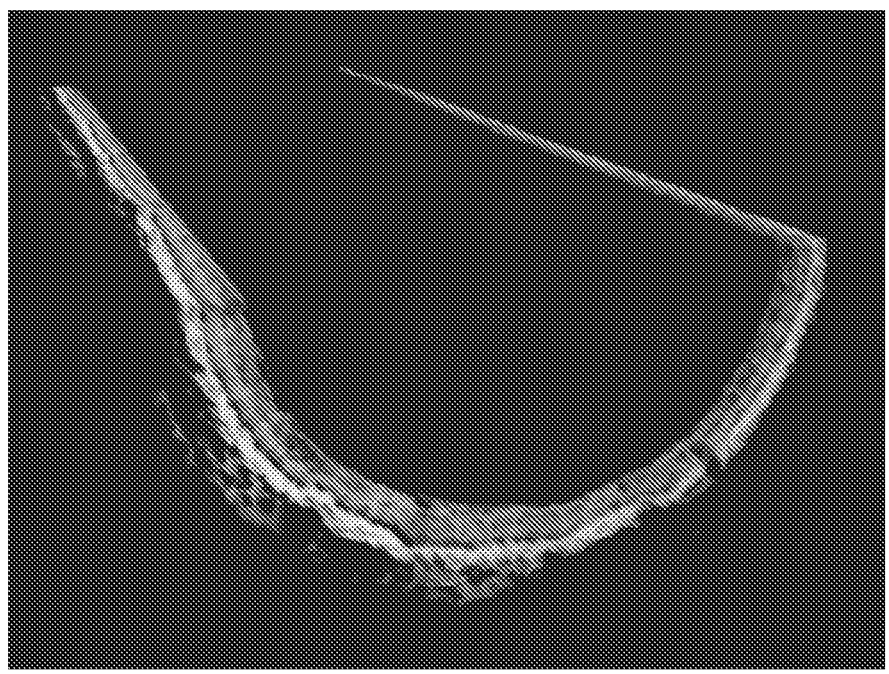

Real time ex vivo imaging study of pig esophagus was performed using the diffractive capsule endoscope along with the SD-OCT system. FIG. 6A illustrate a representative cross-sectional esophageal image acquired by the capsule endoscope with a diffractive lens. The OCT system was running at 17 frames per second (fps) and each frame consisted of about 4,000 A-scans. Layer structures such as epithelium (EP), lamina propria (LP), muscularis mucosa (MM), submucosa (SM), and muscularis propria (MP) layers can be clearly identified on FIG. 6A. 3D imaging was acquired by pulling back the capsule while the beam was circumferentially scanned by the micromotor. A representative reconstructed 3D image is shown in FIG. 6B.

Figure 7:
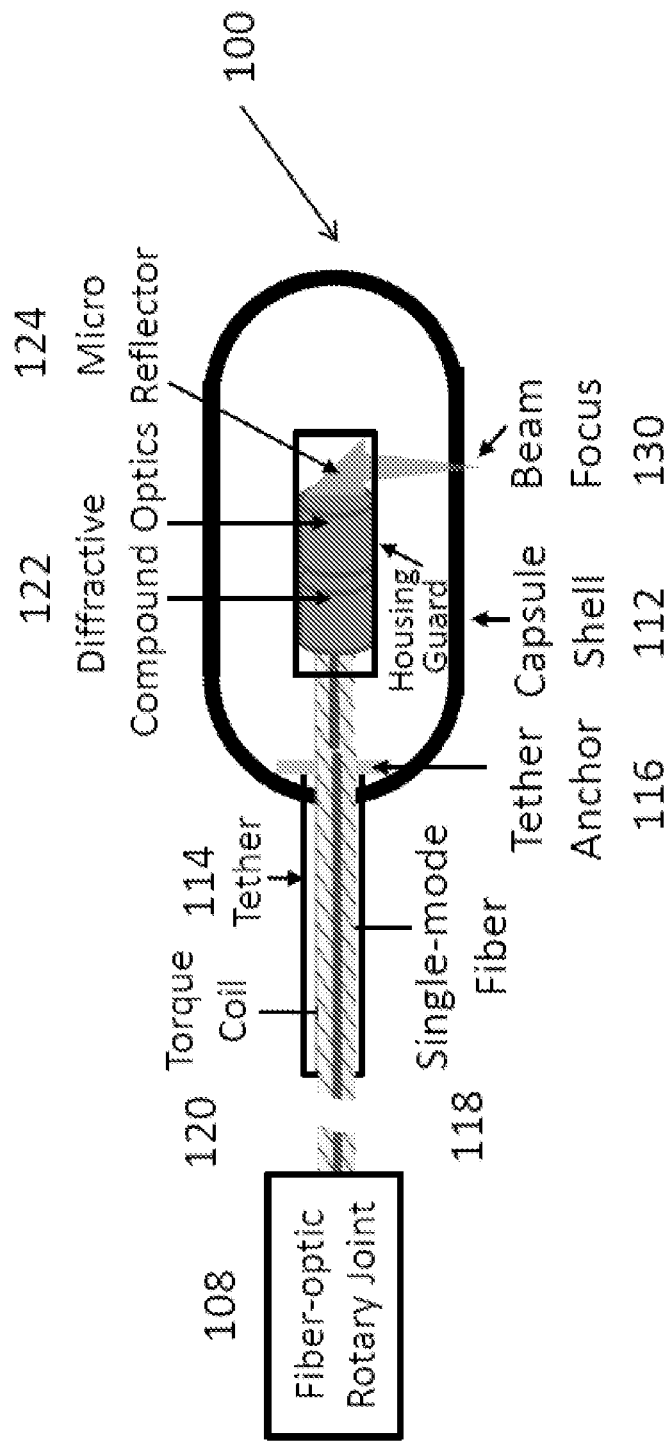
FIG. 7 illustrates a schematic of the distal end of a proximal-scanning OCT capsule probe.

FIG. 7 illustrates a schematic diagram of a distal end design for a proximal-scanning OCT capsule imaging probe 100 with diffractive optics according to an embodiment of the present invention. It entails (not limited to) a broadband fiber-optic rotary joint 108, a capsule 112, a tether 114, a tether anchor 116, a single-mode optical fiber (SMF) 118, a torque coil 120, miniature diffractive optics and a housing guard 122, and a micro beam reflector 124.

Correction of chromatic aberration in the miniature imaging probes becomes very challenging due to the probe size (diameter and rigid length) and cost restriction. Although the concept of using a multi-element lens similar to a microscope objective can be introduced to the miniature OCT imaging probes for correcting the chromatic aberration (as we demonstrated before), that approach would be very challenging and impractical due to prohibitive cost and increased probe size. FIG. 7 also illustrates the point of the beam focus 130 after the beam is reflected off of microreflector 124.

Figure 8:
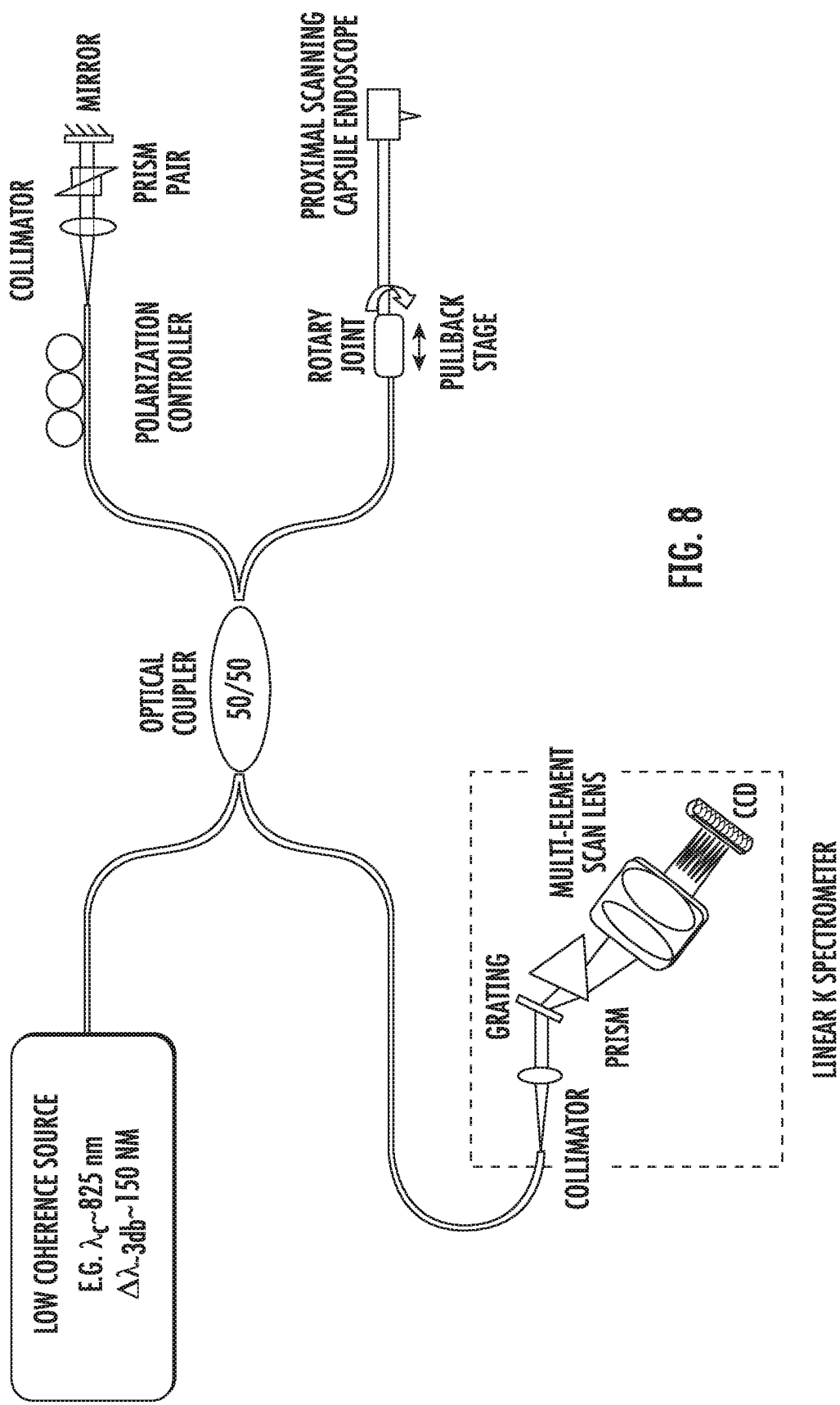
FIG. 8 illustrates a schematic diagram of an 800 nm broadband proximal-scanning capsule SC-OCT system.

FIG. 8 illustrates a schematic a home-built SD-OCT imaging system that can be used with the proximal-scanning, diffractive capsule imaging probe, where a broadband low coherence light source (such as a short pulsed Ti:Sapphire laser) with a 3 dB spectral bandwidth (e.g. of ~150 nm centering at 825 nm) is employed as the light source. The light source is delivered into the sample and reference arms through a broadband 50/50 fiber coupler. In the sample arm, a home-made broadband fiber rotary joint is used to connect the stationary fiber and the capsule in which the distal end optics is to be rotated through a torque coil. The rotary joint is mounted on a translational stage to enable 3D volumetric imaging. In order to match the dispersion in two arms, a prism pair was inserted into reference arm. The residual dispersion mismatch between the two arms can also be numerically compensated. For detection, a custom-designed, home-built linear-in-wavenumber spectrometer is employed. The line scan camera has 2048 pixels and a maximum line scan rate of 70 k/second at 12 bit resolution. Real-time OCT imaging is rendered by a custom C++ program, which controls the system synchronization, real-time data acquisition, signal processing, data storage, etc.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A device for obtaining optical coherence tomography (OCT) images from a subject comprising:
   a miniature OCT capsule, wherein the miniature OCT capsule is sized to obtain OCT images from within the subject
   a light source, wherein the light source comprises a broadband, low-coherence light and a broadband fiber, wherein light from the broadband, low-coherence light is delivered to the miniature OCT capsule via the broadband fiber, and wherein the broadband fiber is coupled to the miniature OCT capsule, such that light from the broadband, low coherence light is transmitted into the miniature OCT capsule;
   diffraction optics configured to mitigate wavelength dependent aberration in the images obtained by the OCT capsule imaging probe, wherein the diffraction optics are positioned within the miniature OCT capsule, and wherein the diffraction optics are configured to bend a longer wavelength more towards an optical axis than a shorter wavelength; and
   a micro reflector, wherein the diffraction optics are positioned within the miniature OCT capsule, wherein the diffraction optics are positioned between the broadband fiber of the light source and the micro reflector, wherein the diffraction optics direct a light beam from the broadband fiber of the light source to the micro reflector, and wherein the micro reflector reflects the light beam such that it can be used for imaging.

2. The device of claim 1 wherein the diffraction optics comprise a diffractive lens.

3. The device of claim 2 wherein the diffractive lens is positioned at a distal end of a compound lens within the OCT capsule imaging probe.

4. The device of claim 2 wherein the diffractive lens comprises a predetermined diffraction efficiency over a predetermined spectral range.

5. The device of claim 4 wherein the predetermined spectral range is 750 nm to 950 nm.

6. The device of claim 1 wherein the wavelength dependent aberration comprises a chromatic aberration.

7. A device for obtaining optical coherence tomography (OCT) images from a subject comprising:
   a miniature OCT imaging capsule, wherein the miniature OCT imaging capsule is sized to obtain OCT images from within the subject;
   a light source, wherein the light source comprises a broadband, low-coherence light and a broadband fiber, wherein light from the broadband, low-coherence light is delivered to the miniature OCT capsule via the broadband fiber, and wherein the broadband fiber is coupled to the miniature OCT capsule, such that light from the broadband, low coherence light is transmitted into the miniature OCT capsule;
   a micromotor beam scanner, wherein the micromotor beam scanner is disposed within the miniature OCT imaging capsule;
   diffraction optics configured to mitigate wavelength dependent aberration in the images obtained by the OCT capsule imaging probe, wherein the diffraction optics are positioned within the miniature OCT capsule, and wherein the diffraction optics are configured to bend a longer wavelength more towards an optical axis than a shorter wavelength; and
   a micro reflector, wherein the diffraction optics are positioned within the miniature OCT capsule, wherein the diffraction optics are positioned between the broadband fiber of the light source and the micro reflector, wherein the diffraction optics direct a light beam from the broadband fiber of the light source to the micro reflector, and wherein the micro reflector reflects the light beam such that it can be used for imaging.

8. The device of claim 7 wherein the diffraction optics comprise a diffractive lens.

9. The device of claim 8 wherein the diffractive lens is positioned at a distal end of a compound lens within the OCT capsule imaging probe.

10. The device of claim 8 wherein the diffractive lens comprises a diffraction efficiency over a specified spectral range.

11. The device of claim 10 wherein the predetermined spectral range is 750 nm to 950 nm.

12. The device of claim 7 wherein the wavelength dependent aberration comprises a chromatic aberration.

13. A device for obtaining optical coherence tomography (OCT) images from a subject comprising:
   a miniature OCT imaging capsule configured to obtain images of the subject, wherein the miniature OCT imaging capsule is sized to obtain OCT images from within the subject;
   a fiber-optic rotary joint, wherein the fiber optic rotary joint is configured to transmit light from a broadband, low-coherence light and a broadband fiber, to the miniature OCT capsule, and wherein the fiber-optic rotary joint is coupled to the miniature OCT capsule, such that light from the broadband, low coherence light is transmitted into the miniature OCT capsule;
   diffraction optics configured to mitigate wavelength dependent aberration in the images obtained by the OCT capsule imaging probe, wherein the diffraction optics are positioned within the miniature OCT capsule, and wherein the diffraction optics are configured to bend a longer wavelength more towards an optical axis than a shorter wavelength; and
   a micro reflector, wherein the diffraction optics are positioned within the miniature OCT capsule, wherein the diffraction optics are positioned between the broadband fiber of the light source and the micro reflector, wherein the diffraction optics direct a light beam from the broadband fiber of the light source to the micro reflector, and wherein the micro reflector reflects the light beam such that it can be used for imaging.

14. The device of claim 13 wherein the diffraction optics comprise a diffractive lens.

15. The device of claim 14 wherein the diffractive lens is positioned at a distal end of a compound lens within the OCT capsule imaging probe.

16. The device of claim 14 wherein the diffractive lens comprises a predetermined diffraction efficiency over a predetermined spectral range.

17. The device of claim 16 wherein the predetermined spectral range is 750 to 950 nm.

18. The device of claim 13 wherein the wavelength dependent aberration comprises a chromatic aberration.

\* \* \* \* \*